United States Patent
Wieczorek et al.

(10) Patent No.: US 8,692,681 B2
(45) Date of Patent: Apr. 8, 2014

(54) DYNAMIC PET IMAGING WITH ISOTOPE CONTAMINATION COMPENSATION

(75) Inventors: Herfried Wieczorek, Aachen (DE); Frank O. Thiele, Seattle, WA (US); Manoj V. Narayanan, Snohomish, WA (US)

(73) Assignee: Koninklijke Philips N.V., Eindhoven (NL)

( * ) Notice: Subject to any disclaimer, the term of this patent is extended or adjusted under 35 U.S.C. 154(b) by 172 days.

(21) Appl. No.: 13/382,191

(22) PCT Filed: Jun. 15, 2010

(86) PCT No.: PCT/IB2010/052671
§ 371 (c)(1), (2), (4) Date: Jan. 4, 2012

(87) PCT Pub. No.: WO2011/004273
PCT Pub. Date: Jan. 13, 2011

(65) Prior Publication Data
US 2012/0098671 A1 Apr. 26, 2012

Related U.S. Application Data

(60) Provisional application No. 61/223,422, filed on Jul. 7, 2009.

(51) Int. Cl.
*G08B 21/00* (2006.01)
(52) U.S. Cl.
USPC .................. 340/679; 340/686.4; 340/691.1
(58) Field of Classification Search
USPC ............. 340/679, 680, 673–675, 678, 690, 340/686.4–686.5, 691.1, 691.6, 692
See application file for complete search history.

(56) References Cited

U.S. PATENT DOCUMENTS

| | | | |
|---|---|---|---|
| 5,598,449 A | 1/1997 | Yamazaki et al. | |
| 6,858,850 B2 | 2/2005 | Williams et al. | |
| 2005/0167599 A1* | 8/2005 | Schlyer et al. | 250/363.03 |
| 2005/0239104 A1* | 10/2005 | Ferea et al. | 435/6 |
| 2007/0260138 A1* | 11/2007 | Feldman et al. | 600/409 |
| 2008/0230703 A1* | 9/2008 | Kadrmas et al. | 250/363.03 |
| 2008/0280774 A1* | 11/2008 | Burczynski et al. | 506/9 |
| 2010/0016715 A1* | 1/2010 | Gagnon et al. | 600/436 |
| 2011/0288407 A1* | 11/2011 | Brinks et al. | 600/427 |

OTHER PUBLICATIONS

Glatting, G., et al.; Treatment of radioactive decay in pharmacokinetic modeling: Influence on parameter estimation in cardiac 13N-PET; 1999; Med. Phys.; 26(4)616-621.

(Continued)

*Primary Examiner* — Daniel Previl

(57) ABSTRACT

A nuclear imaging system includes a scanner (8), such as a PET scanner. A patient is injected with a [$^{13}$N]ammonia radioisotope tracer which is contaminated with a small percent of $^{18}$F contamination. The scanner receives radiation from the injected tracer and a reconstruction processor (28) reconstructs the detected radiation into image representations. A calibration processor (16) generates an estimated decay curve based on the proton bombardment and a priori information about the tracer. An activity meter (42) measures radiation emitted from a sample of the tracer and a dose calibrator (44) determines a decay curve from the measured radiation. The detected radiation is corrected with one of the decay curves during reconstruction or a correction processor (50) corrects reconstructed images with one or both of the decay curves. A display (14) displays uncorrected reconstructed images and the decay curve and/or the corrected images.

20 Claims, 5 Drawing Sheets

(56) References Cited

OTHER PUBLICATIONS

Huang, S. C., et al.; An Investigation of a Double-Tracer Technique for Positron Computerized Tomography; 1982; J. of Nuclear Medicine; 23(9)816-822.

Wilson, J. W., et al.; Optimizing Sequential Dual Tracer P.E.T. Studies Using a Combined 2D/3D Imaging Protocol; 2004; IEEE Nuclear Science Symposium Conf. Record; pp. 3357-3360.

* cited by examiner

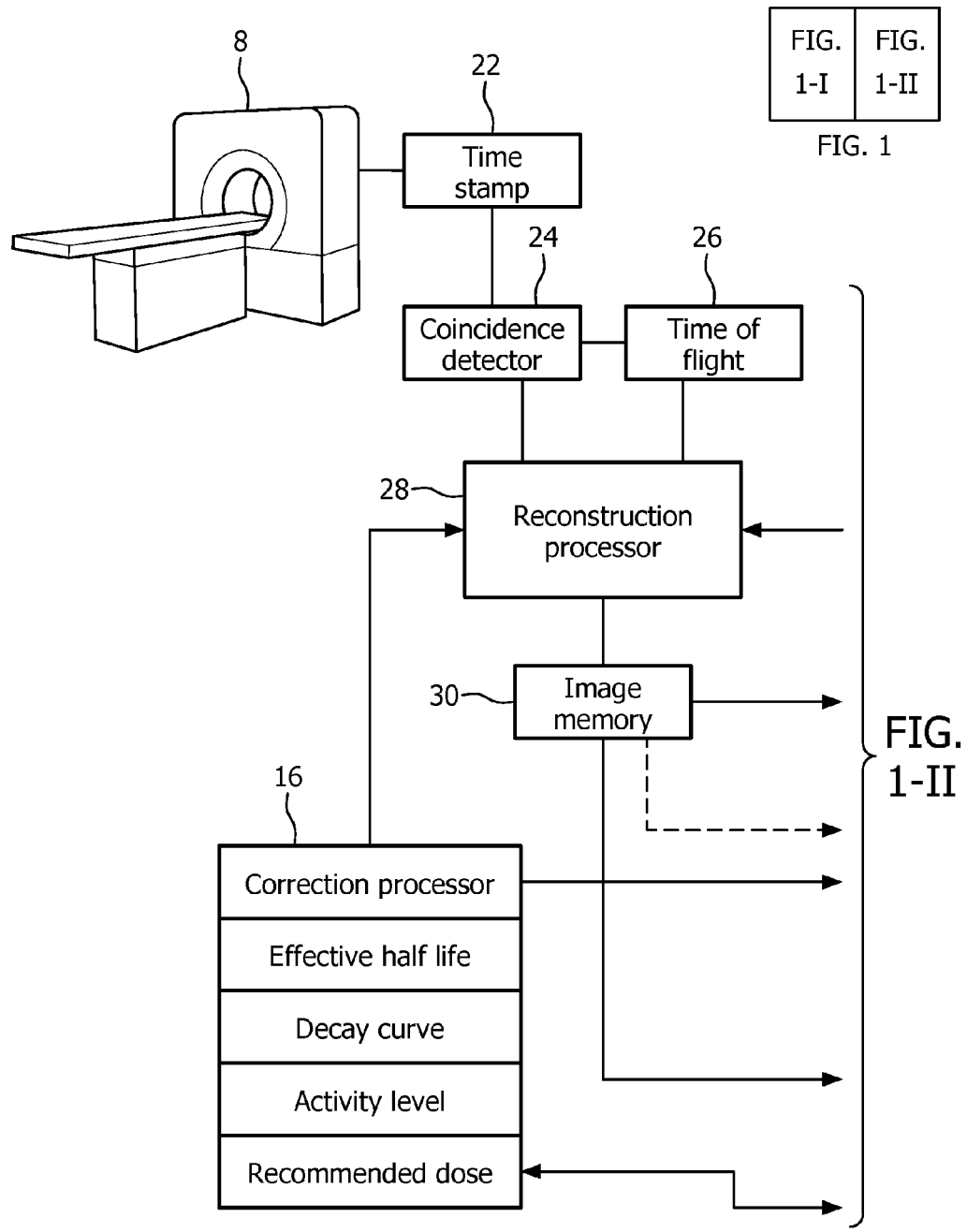
FIG. 1-I

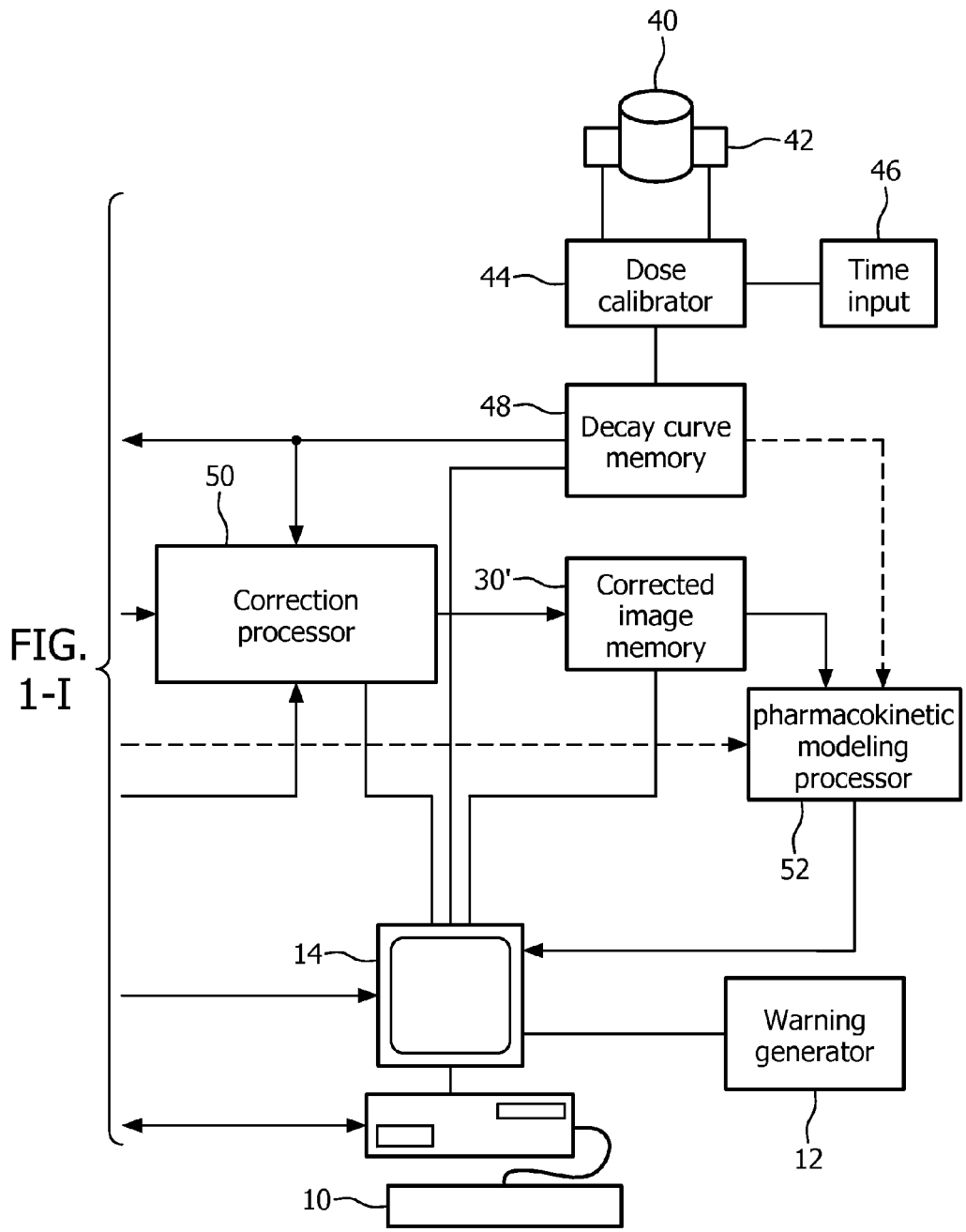
FIG. 1-II

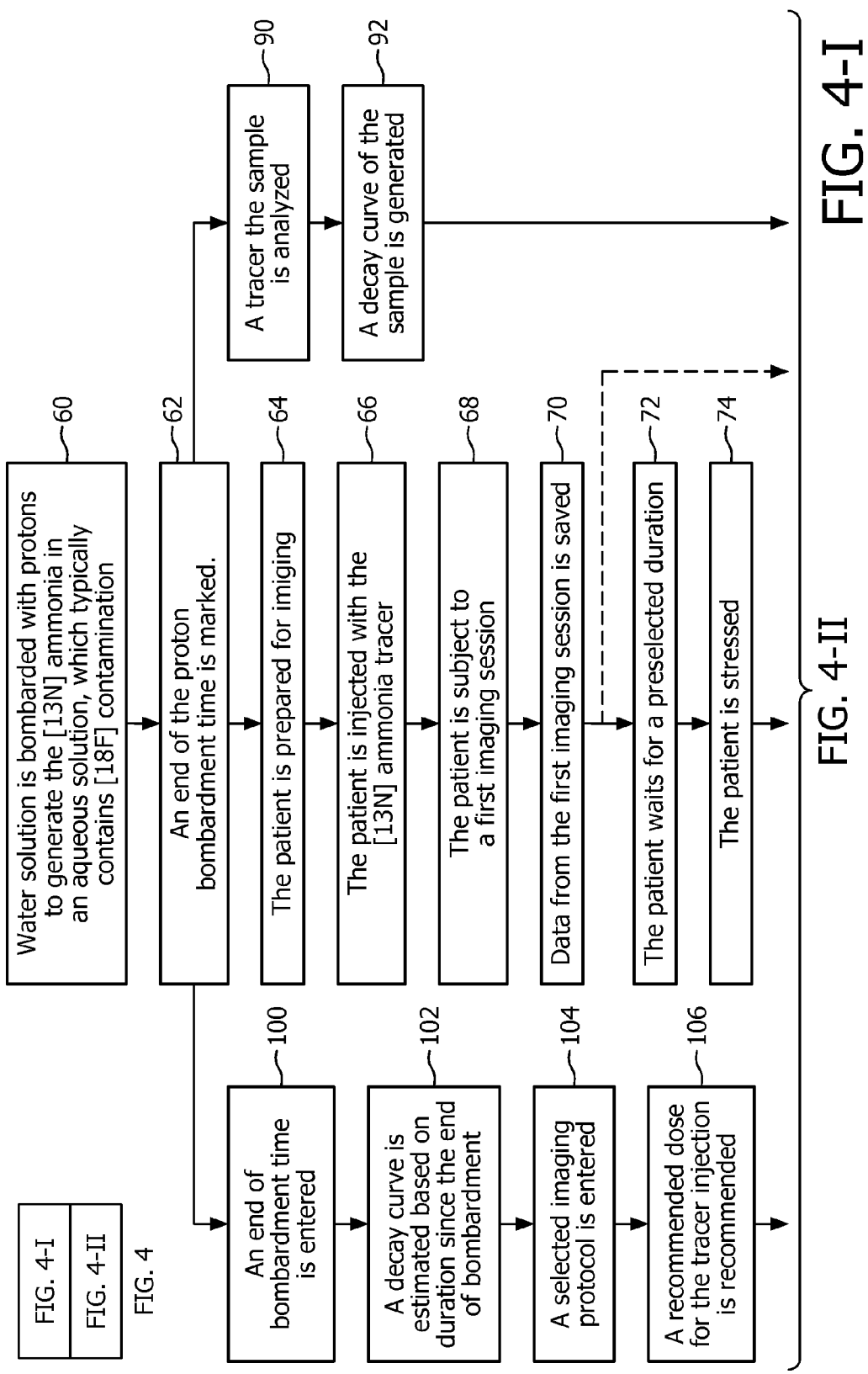

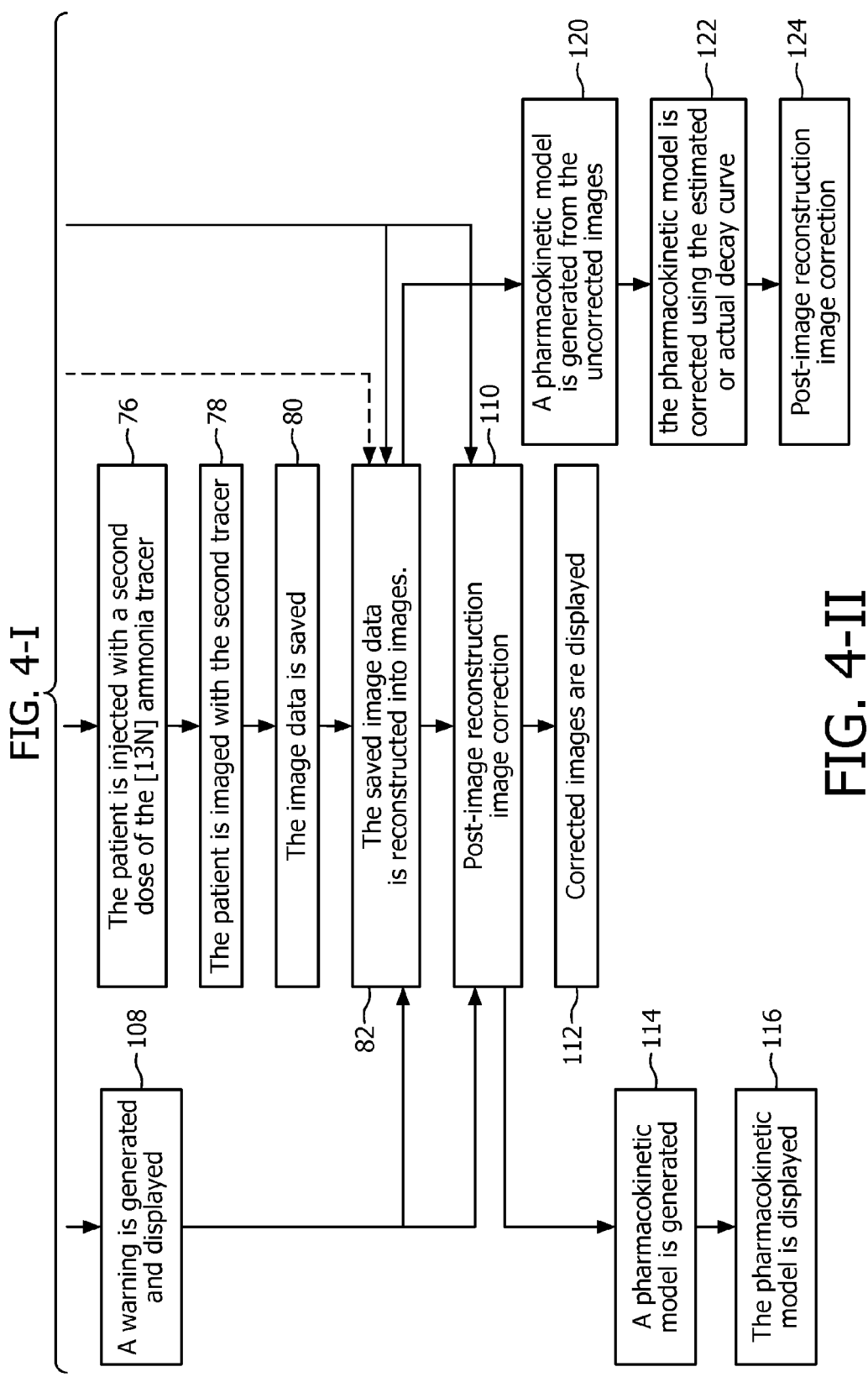

US 8,692,681 B2

DYNAMIC PET IMAGING WITH ISOTOPE CONTAMINATION COMPENSATION

CROSS REFERENCE TO RELATED APPLICATIONS

This application claims the benefit of U.S. provisional application Ser. No. 61/223,422 filed Jul. 7, 2009, which is incorporated herein by reference.

The present application relates to the nuclear imaging arts. It finds particular application with uptake studies in conjunction with positron emission tomography (PET) imaging. However, it is to be appreciated that it will have utility in conjunction with other types of PET imaging, single photon emission CT (SPECT) imaging, and the like.

When performing an uptake study, such as assessing myocardial blood flow for diagnosing coronary artery disease (CAD), the subject is injected with a radioactive tracer and imaged at rest. Then after an appropriate interval, the patient is stressed either through an exercise protocol (treadmill) or pharmacologically (intravenous infusion of dipyridamole for example), injected with another dose of the radioactive tracer, and imaged under a stress situation. The more widely used clinical rest/stress protocols are 1-day protocols using SPECT imaging ($^{201}$Tl for rest and $^{99m}$Tc-MIBI for stress). However, myocardial perfusion studies with PET tracers such as [$^{13}$N]ammonia ($NH_3$) offer several potential advantages over SPECT protocols including: higher spatial resolution, higher scanner sensitivity and shorter acquisition times.

$^{13}$N is an advantageous isotope for performing such uptake studies because $^{13}$N has a half-life of about 10 minutes. Because the 20-30 minute waiting period is 2-3 half-lives, first dose of the radioactive tracer significantly decays before the second imaging session. Subsequently, it is feasible to perform rest-stress imaging protocols with [$^{13}$N]ammonia in 60-90 min representing a significant time-reduction over typical clinical protocols.

[$^{13}$N]ammonia is typically generated in the hospital or other medical care institution, commonly by proton bombardment of watery solutions. Typically, there is a small percentage, e.g., 0.1% contamination at the end of the bombardment with other radioactive isotopes, particularly $^{18}$F. The present inventors have recognized that this small initial percentage of $^{18}$F contamination can lead to significant errors in the interpretation of the resultant images. $^{18}$F has a half-life of about 110 minutes. Due to the 10 minute versus 110 minute difference in half-lives, the percentage contamination of the $^{18}$F isotope grows over time, i.e., during the course of an imaging session. For example, at 85 minutes after the end of the proton bombardment, the contamination level of $^{18}$F is 21%. Due to the transport time from the cyclotron to the imaging suite and the duration of the imaging sessions, 85 minutes from the end of bombardment, the high level of $^{18}$F contamination can be within the imaging window.

The present application proposes to address these problems and others.

In accordance with one aspect, a nuclear imaging system is provided. A scanner receives radiation from a tracer injected into a subject, which tracer includes at least a primary radioisotope component and one or more contamination radioisotope component(s). A reconstruction processor reconstructs the detected radiation into image representations. The system includes at least one of (1) an uptake correction processor which corrects the reconstructed images and/or the detected radiation in accordance with a decay curve of the radioisotope contaminated tracer and/or (2) a calibration processor which determines the decay curve of the radioisotope contaminated tracer. A display displays at least one of (1) the reconstructed image representation corrected for the decay curve of the tracer and/or (2) the reconstructed image without correction and the decay curve of the tracer to enable a diagnostician to correct the uncorrected images during analysis.

In accordance with another aspect, a method of nuclear imaging is provided. A radioisotope tracer is generated by proton bombardment, which tracer has a primary radioisotope component and is contaminated with at least one other radioisotope. The tracer is injected into a subject. Radiation emitted by the tracer injected into the subject is detected. The detected radiation is reconstructed into an image representation. A decay curve for the tracer is generated.

In accordance with another aspect, a computer-readable medium is provided. The computer-readable medium stores a program which controls a computer. The controlled computer generates a decay curve for a radioisotope tracer which is generated by proton bombardment, which tracer has a primary radioisotope component and is contaminated with at least one other radioisotope. The computer is further controlled to reconstruct images of a subject injected with the radioisotope and generate a display of at least one of (1) the reconstructed images and the generated decay curve and/or (2) reconstructed images corrected in accordance with the decay curve.

One advantage resides in improved accuracy in evaluating the results of uptake studies.

Another advantage resides in compensation for other isotope contamination in radioactive tracers.

Still further advantages will become apparent to those of ordinary skill in the art upon reading and understand the following detailed description.

The innovation may take form in various components and arrangements of components, and in various steps and arrangements of steps. The drawings are only for purposes of illustrating various aspects and are not to be construed as limiting the invention.

FIG. 1 is a diagrammatic illustration of a nuclear imaging system in accordance with the present innovation;

Figure 2:
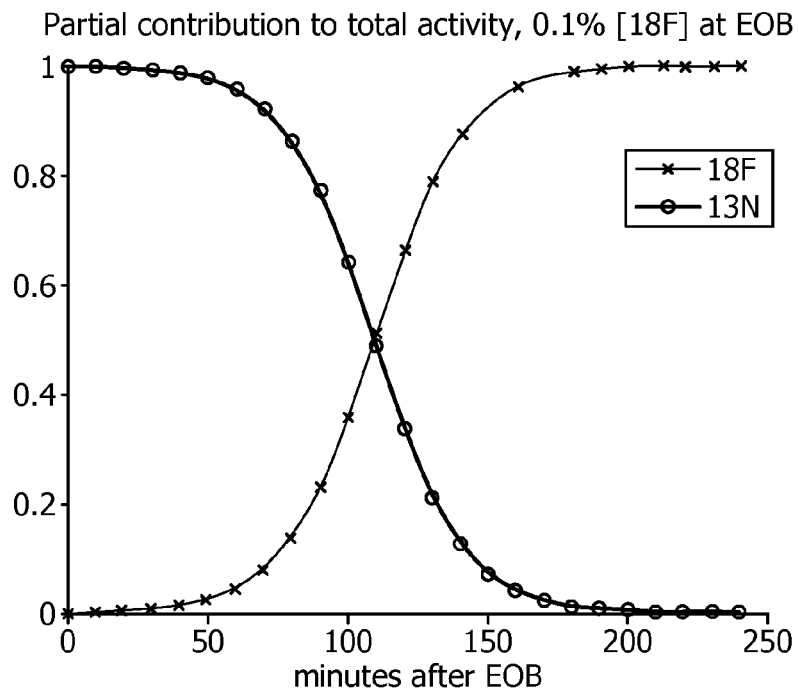
FIG. 2 illustrates the partial contribution to total activity over time for [$^{13}$N]ammonia contaminated with $^{18}$F.

In preparing a tracer at a medical imaging facility, a dose of [$^{13}$N]ammonia is generated by proton bombardment. The tracer is transported to an imaging suite and injected into a patient to be imaged. With reference to FIG. 1, the patient injected with the [$^{13}$N]ammonia is disposed in a nuclear imaging device 8, such as a PET scanner. In one example, the patient remains in the scanner for 6-10 minutes to generate a first set of imaging data. After 20-30 minutes, the patient is injected with a second dose of the radioactive tracer from the same batch and imaged again. In other imaging protocols, the patient is given only one dose of the tracer and the uptake and/or washout is monitored over an extended duration, e.g., 20-40 minutes.

During the initial scan set up, the technician inputs the selected scan protocol with an input device 10 of a graphic user interface. When the protocol includes use of a [$^{13}$N] ammonia tracer, a warning generator 12 generates a warning concerning the $^{18}$F contamination which is displayed on a display 14 of the user interface. The warning warns the clinician to consider the purity of the [$^{13}$N]ammonia and the count rate limitations of the PET scanner, and the like. The user is also prompted to check the production method for the [$^{13}$N] ammonia or other indicators of the level of contamination.

The display also prompts the user to enter the actual time of the end of the bombardment or other indication of the durations between the end of bombardment and the commencing of imaging. Optionally, the user may also be prompted to enter the level of initial contamination of the tracer sample. The warning may also include tables, graphs, or other information which helps the diagnostician correctly interpret the images.

In one embodiment, a calibration processor 16 uses the contamination and end of bombardment time to calculate an effective half-life of the tracer, which effective half-life can be used by the diagnostician for decay correction. The system further checks the effective half-life by monitoring a singles rate during imaging and notifying the user if the effective half-life estimate deviates from the estimate based on known contamination. The correction processor 16 further retrieves a precalculated decay curve for display. From the end of bombardment, the calibration processor calculates the activity level of the [$^{13}$N]ammonia and displays the activity level to enable the user to select proper imaging settings. In one embodiment, the calibration processor further calculates tracer dose recommendations for the selected imaging protocol, which recommended dose is also displayed on the display 14.

During the imaging session, the nuclear scanner 8, a PET scanner in the present embodiment, detects radiation events. The radiation events are time-stamped by a time-stamping device 22. A coincidence detector 24 detects coincident pairs of radiation events which define a line of response between the coincident pairs. Optionally, a time of flight processor 26 localizes the coincident events along the line of response. A reconstruction processor 20 reconstructs the lines of response into a series of image representations stored in an image memory 30.

In one embodiment, the generated diagnostic images from the two or more studies are displayed to the clinician or diagnostician, for example on the display 14. The clinician uses the effective half-life information and the decay curve to interpret the images accurately.

In another example, a portion of the tracer 40 is placed in an activity meter 42. The activity meter monitors the radioactivity of the reference sample of the radioactive tracer over time. Preferably, the activity meter starts this measurement prior to imaging and continues it after the imaging session has concluded. In the case of positron emitting isotopes which also emit single gamma quanta, the activity meter preferably uses coincidence detection, e.g., one or more pairs of radiation detectors with a coincidence detector, in order to remove the single gamma contamination. Alternately, singles and other stray radiation is filtered using energy discrimination to eliminate radiation other than 511 keV photons. A dose calibrator 44 receives the end of bombardment or other indicator of duration since the end of the bombardment from the input device 10 or a time input device 46 associated with the activity meter. Based on this information, the dose calibrator 44 calculates a decay curve of the actual sample of the tracer being used in each imaging session, which decay curve is stored in a decay curve memory 48. If the method of manufacture, the initial contamination level, and the like are known, only a very limited number of points, e.g., two, along the decay curve are necessary to scale a known or nominal decay curve appropriately. On the other hand, by taking a larger plurality of points, the decay curve can be calculated accurately without knowing the initial radiation isotope contamination levels of the sample, the nature of the contaminating isotopes, or the like.

The decay curve from the decay curve memory 48 or the decay curve from the calibration processor 16, in one embodiment, is provided to the reconstruction processor 28 and used to make corrections during reconstruction. In another embodiment, a correction processor 50 receives the decay curve from the calibration processor 16 or the decay curve memory 48 and corrects previously generated images in the image memory 30 to generate corrected images which are stored in the same or a different corrected image memory 30□.

In another embodiment, the estimated decay curve from the calibration processor 16 is provided to the reconstruction processor 28 such that the reconstructed images have a preliminary correction. In another embodiment, the correction processor 50 determines the difference or error between the estimated decay curve from the calibration processor 16 and the actual decay curve from the memory 48 and adjusts the preliminarily corrected images accordingly in a post reconstruction correction.

In another embodiment, a pharmacokinetic modeling processor 52 analyzes the temporally displaced images in the image memory 30' and fits a pharmacokinetic model parameters to the data. Alternately, the pharmacokinetic model can be adjusted with the actual decay curve and uncorrected data from memory 30 fitted to the adjusted pharmacokinetic model. The uncorrected images, the corrected images, the pharmacokinetic models, the various decay curves, and the like are displayable to the clinician, the radiologist, and others on an appropriate display, such as display 14, or saved to memory, such as a hospital-wide database.

Figure 3:
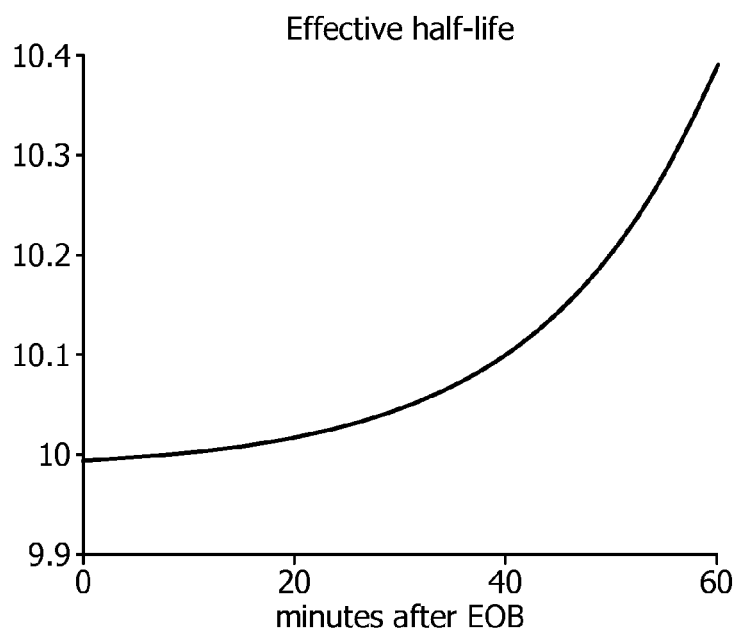
FIG. 3 illustrates the effective half-life of a [$^{13}$N]ammonia tracer contaminated with $^{18}$F; and, FIG. 4 illustrates a method of nuclear imaging.

FIG. 2 illustrates the partial contribution to total activity of $^{18}$F versus $^{13}$N over time. FIG. 3 illustrates an effective half-life curve over time. As will be noted on the effective half-life curve, as the $^{13}$N decays and the $^{18}$F becomes a higher proportion of the tracer, the effective half-life elongates.

A plurality of processors are described and named for simplicity of describing the processing operations. It is to be appreciated that the processing operations can be performed by a single processor, divided among more processors, or be performed by a different grouping of processors without departing from the present invention.

Although described with reference to $^{18}$F contamination of [$^{13}$N]ammonia, it is to be appreciated that various other types of contamination radiation may be found in other radioactive tracers and radioactive tracers made by other techniques.

With reference to FIG. 4, at step 60, an aqueous solution is bombarded with protons to generate the [$^{13}$N]ammonia and water solution, which typically contains $^{18}$F contamination. At step 62, an end of the proton bombardment time is marked. At step 64, the patient is prepared for imaging, and at step 66, the patient is injected with the [$^{13}$N]ammonia tracer. At step 68, the patient is subject to a first imaging session and at step 70, data from the first imaging session is saved. In an exemplary stress test protocol, at step 72, the patient waits for a preselected duration, typically long enough for a significant portion of the tracer from the first injection to be washed out of the patient's system. In the stress test embodiment, the patient is stressed at step 74. At step 76, the patient is injected with a second dose of the [$^{13}$N]ammonia tracer. At step 78, the patient is imaged with the second tracer and the image data is saved at step 80. At step 82, the saved image data is reconstructed into images. Of course, other protocols are also envisioned including some with a single imaging session, e.g. moving from step 70 directly to step 82.

In one embodiment, when the tracer arrived at the imaging suite, the sample was analyzed at step 90. The analysis, in one embodiment, starts before the first imaging session and continues until after the second imaging session. At step 92, a decay curve of the sample used in imaging is generated.

In another embodiment, during the preparation of the patient, at step 100, an end of bombardment time is entered and at step 102, a decay curve is estimated based on duration since the end of bombardment. At step 104, a selected imaging protocol is entered. At step 106, a recommended dose for the tracer injection is recommended. At step 108 a warning is generated and displayed The resultant images can be corrected using the estimated decay curve from step 104 or the actual decay curve generated at step 92, either during the image reconstruction step 82 or in a post-image reconstruction image correction step 110. The corrected images are displayed at step 112. In another embodiment, at step 114, a pharmacokinetic model is generated and at step 116, the model is displayed. In another embodiment, in a step 120, a pharmacokinetic model is generated from the uncorrected images. At step 122, the pharmacokinetic model is corrected using the estimated or actual decay curve. At step 124, the pharmacokinetic model is displayed.

In accordance with another aspect, a computer-readable medium, such as a DVD, CD, tape, other portable medium, computer memory, and the like is programmed with appropriate programming steps or software in order to control one or more processors to perform one or more of the computer implementable steps described above.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A nuclear imaging system comprising:
   a scanner which detects radiation from a radioisotope contaminated tracer injected into a subject, which tracer includes at least one primary radioisotope component and one or more contamination radioisotope components;
   a reconstruction processor which reconstructs the detected radiation into image representations;
   at least one of (1) an uptake correction processor which corrects the reconstructed images and the detected radiation in accordance with a decay curve of the radioisotope contaminated tracer and/or (2) a processor which determines the decay curve of the radioisotope contaminated tracer; and
   a display which displays at least one of (1) a reconstructed image representation corrected for the decay curve of the tracer and/or (2) a reconstructed image without correction and the decay curve of the tracer to enable a diagnostician to correct the uncorrected images during analysis.

2. The apparatus according to claim 1, further including:
   an input on which a clinician inputs a selected imaging protocol; and
   a warning generator which generates a warning on the display in response to the clinician selecting an imaging protocol utilizing a radioisotope contaminated tracer.

3. The apparatus according to claim 1, wherein the tracer is created by proton bombardment which creates the primary radiation component and the contamination radiation component, the contamination radiation component having a longer half-life than the primary radiation component such that a percentage of the contamination radiation component grows with time and wherein the processor receives an indication of a time since an end of the proton bombardment and generates the decay curve of the radioisotope contaminated tracer which is communicated to at least one of the display and the correction processor.

4. The apparatus according to claim 1, wherein the processor further generates a recommended dose of the tracer.

5. The apparatus according to claim 1, further including:
   a warning generator which generates a warning on the display in response to the clinician selecting an imaging protocol which uses a radioisotope contaminated tracer.

6. The apparatus according to claim 1, further including
   an activity meter which receives a sample of the tracer and measures radiation emitted therefrom;
   a dose calibrator which determines the decay curve from the measured radiation; and
   a decay curve memory which stores the determined decay curve, the decay curve memory being connected with at least one of the reconstruction processor and the correction processor.

7. The apparatus according to claim 1, further including:
   a pharmacokinetic modeling processor which analyzes the reconstructed diagnostic images which have been corrected by the uptake correction processor and applies corrected uptake data to a pharmacokinetic model.

8. The apparatus according to claim 1, wherein the primary radioactive component of the tracer is [$^{13}$N]ammonia and the contamination radiation is $^{18}$F.

9. A method of nuclear imaging comprising:
   detecting radiation emitted by a radioisotope tracer injected into the subject, which radioisotope tracer is generated by proton bombardment, the tracer having a primary radioisotope component and being contaminated with at least one other radioisotope;
   reconstructing the detected radiation into an image representation; and,
   generating a decay curve for the tracer.

10. The method according to claim 9, further including:
    generating diagnostic images corrected in accordance with the decay curve to compensate for the contamination radioisotope component in the tracer and displaying the corrected diagnostic images.

11. The method according to claim 9, further including:
    inputting a selected imaging protocol; and
    generating a warning on a display in response to the clinician selecting an imaging protocol utilizing the tracer which includes a contamination isotope.

12. The method according to claim 9, further including:
    receiving an indication of a time since the end of the proton bombardment which created the contaminated tracer; and
    generating the decay curve based on the time since the end of the bombardment.

13. The method according to claim 9, further including:
    after a selected duration which is sufficiently long for the primary radiation component to wash out of the subject, injecting the subject with a second dose of the radioisotope generated by a second proton bombardment;
    detecting radiation from the second dose of the radioisotope and residual primary radiation and contamination radiation from the earlier radioisotope tracer injection;
    reconstructing the detected radiation into subsequent images; and
    compensating the subsequent images with the decay curve.

14. The method according to claim 9, further including:
displaying the diagnostic images and the deca curve to enable a diagnostician to correct an analysis of the diagnostic images to compensate for the contamination isotope in the tracer.

15. The method according to claim 9, further including:
measuring radiation emitted from a sample of the tracer; and,
determining the decay curve from the measured radiation.

16. The method according to claim 14, further including:
correcting the reconstructed diagnostic images in accordance with the decay curve; and
fitting uptake data derived from the corrected diagnostic images to a pharmacokinetic model.

17. The method according to claim 9, wherein the primary radioisotope component has a half-life which is shorter than a half-life of the contamination isotope.

18. The method according to claim 9, wherein the primary radioactive component of the tracer is [$^{13}$N]ammonia and the contamination radiation is $^{18}$F.

19. A non-transitory computer-readable medium storing a computer program which controls a computer to:
generate a decay curve for a radioisotope tracer which is generated by proton bombardment, the tracer having a primary radioisotope component and being contaminated with at least one other radioisotope, the primary radiation component having a shorter half-life than the other isotope such that a percentage of the other isotope increases in time;
reconstructing a series of images at selected intervals of a subject injected with the radioisotope; and,
generating a display of at least one of (1) the reconstructed images and the generated decay curve, and (2) the reconstructed images corrected in accordance with the decay curve.

20. A nuclear imaging system comprising:
a scanner which detects radiation from a radioisotope contaminated tracer injected into a subject, which tracer includes at least one primary radioisotope component and one or more contamination radioisotope components;
an input on which a clinician inputs a selected imaging protocol; and
one or more processors configured to:
reconstruct detected radiation into image representations;
at least one of (1) correct the reconstructed images and/or the detected radiation in accordance with a decay curve of the radioisotope contaminated tracer and/or (2) determine the decay curve of the radioisotope contaminated tracer; and
generate a warning on the display in response to the clinician selecting an imaging protocol utilizing the radioisotope contaminated tracer on a display.

\* \* \* \* \*